(12) United States Patent
Edgar

(10) Patent No.: US 6,675,803 B1
(45) Date of Patent: Jan. 13, 2004

(54) EPISIOTOMY OR PERINEAL TEAR SHIELD FOR USE DURING URINATION

(76) Inventor: Tommie G. Edgar, 903 Meadowhaven Dr., Harrison, AR (US) 72601

( * ) Notice: Subject to any disclaimer, the term of this patent is extended or adjusted under 35 U.S.C. 154(b) by 95 days.

(21) Appl. No.: 09/867,302

(22) Filed: May 29, 2001

(51) Int. Cl.[7] ................................................ A61F 6/06
(52) U.S. Cl. ...................................... 128/830; 128/846
(58) Field of Search ................................ 128/845, 846, 128/869, 830; 604/329, 346

(56) References Cited

U.S. PATENT DOCUMENTS 4,911,698 A * 3/1990 Wapner ...................... 604/329
5,983,410 A * 11/1999 Webster ........................ 4/300.3
2001/0044613 A1 * 11/2001 Stephenson ............ 604/385.01

* cited by examiner

*Primary Examiner*—Michael A. Brown
(74) *Attorney, Agent, or Firm*—Keisling & Pieper PLC; Trent C. Keisling; David B. Pieper

(57) ABSTRACT

A protective device particularly suited for use by females after childbirth generally characterized by a plastic shield for protecting the episiotomy or perineal tear surface from urine flow while urinating over the toilet. The device consists of a sole concave interior (20) plastic with adjacent handle (10) and contoured upper lip (22) adaptable to the female genitalia to be placed between the episiotomy or perineal tear surface and the urethra to alleviate the painful contact of urine on the wound and to promote healing.

15 Claims, 1 Drawing Sheet

EPISIOTOMY OR PERINEAL TEAR SHIELD FOR USE DURING URINATION

CROSS-REFERENCE TO RELATED APPLICATIONS

Not Applicable

STATEMENT REGARDING FEDERALLY SPONSORED RESEARCH FOR DEVELOPMENT

Not Applicable

REFERENCE TO A MICROFICHE APPENDIX

Not Applicable

BACKGROUND OF INVENTION

This invention generally relates to the use of a shield against the perineum, more specifically by protecting episiotomies and perineal tears occurring during childbirth from contact with urine while urinating.

The perineum inclusive of the vulva, perineum and anus is generally compromised during childbirth, especially when the vaginal opening is too small for the birth of an infant. There are two common practices. The first is a surgical procedure known as an episiotomy, an incision made in the perineum between the vaginal opening and the anus to facilitate delivery of the baby. The second is the tear of the perineum, which contains no surgical procedure, but allows the skin to stretch until it separates allowing birth of baby. With both the episiotomy and perineal tear, tissue damage causes bruising, swelling and slow healing and accounts for a great deal of pain and discomfort, especially during urination. Urine is acidic and makes the raw skin sting. Common practice to relieve this pain is by pouring warm water over wound surface while urinating. Or by urinating into water held in such apparatus as a bathtub. Urine has been known to carry infectious material, which causes slower healing and possibly infection to wound. The above merely dilutes the urine but does not provide adequate pain relief or protection from infection. This invention shields the episiotomy or perineal tear from the contact of urine completely. By grasping the handle and holding the plastic elongated concaved shield in front of the wound, thus protecting it, while urinating over the toilet or in a standing position no urine is able to spray on the wound.

BRIEF SUMMARY OF THE INVENTION

Accordingly, several objects and advantages of my invention are:

(a) to provide protection to the episiotomy or perineal tear from urine;
(b) to promote healing through the prevention of foreign substances found in urine to contact wound;
(c) to provide a portable means of protection for use anywhere;
(d) to provide an easy to use handle that provides protection to left or right handed female;
(e) to provide a more sanitary form of protection;
(f) to provide a reusable and disposable shield;
(g) to provide a shield useful in different positions;
(h) to provide a shield which can be manufactured simply and inexpensively;
(i) to provide a shield to alleviate pain caused by urine.

Further objects and advantages are to provide a shield which can be used easily and conveniently to protect wound, without damaging the perineum, which is simple to use and inexpensive to manufacture, which can be used immediately by any female after childbirth, in different position and anywhere, which can be used repeatedly and disposable, which can alleviate pain and provides a source of healing by eliminating urine contact with wound. Still further objects and advantages will become apparent from a consideration of the ensuing description and drawings.

REFERENCE NUMERALS IN DRAWINGS

| | |
|---|---|
| 10 handle | 12 top of shield |
| 14 rounded back | 16 bottom of shield |
| 18 sides | 20 concaved interior |
| 22 contoured lip | |

DETAILED DESCRIPTION OF THE INVENTION

Figure 1:
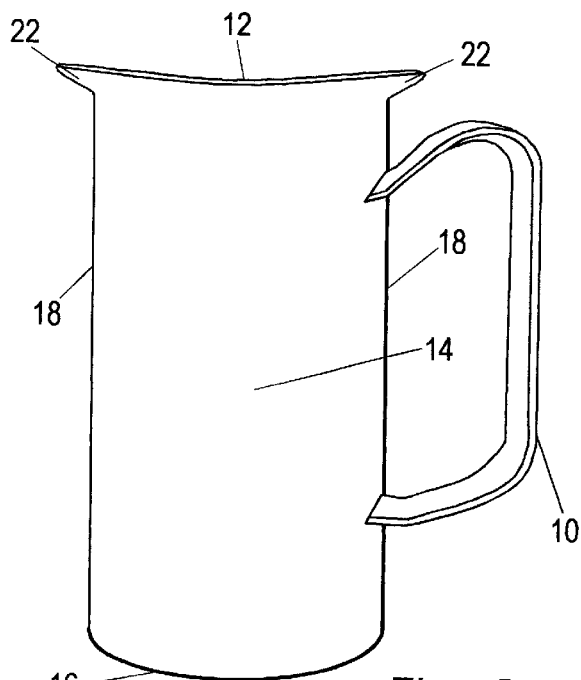
FIG. 1 shows a rear view of the shield with a handle on the right constructed according to the invention.
Figure 4:
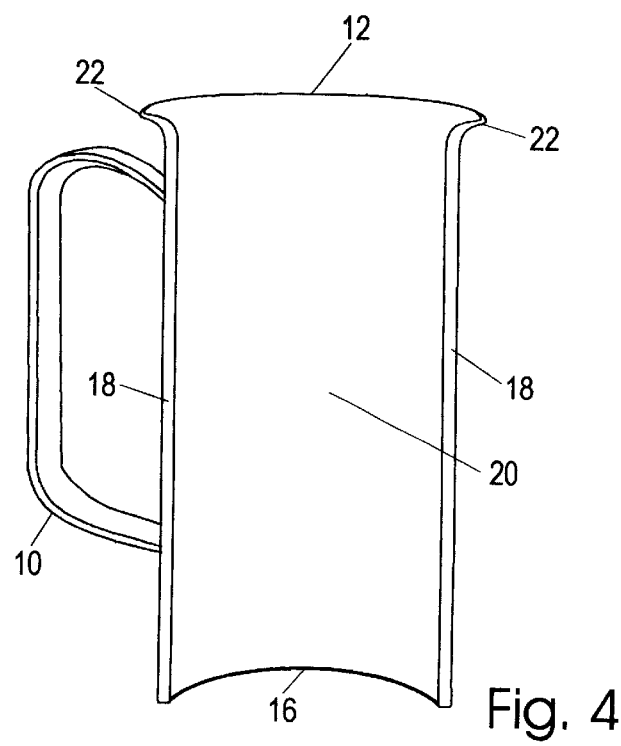
FIG. 4 shows a plan view of the shield with a concaved interior and contoured top lip constructed according to the invention.

A typical embodiment of the shield of my invention is illustrated in FIG. 4 (plan view) and FIG. 1 (rear view). The shield is made of suitable smooth semi-rigid material that can be repeatedly reused having a curved base 16 with ascending beveled outer sides 18 with affixed adjacent C-shaped handle 10 and a rounded back 14. Adjoining the outer sides 18 is a contoured lip 22, which completes a rounded top 12. FIG. 4 shows a front view or plan view with elongated concaved interior 20 with adjacent C-shaped handle 10 to the left. In the preferred embodiment, the shield is smooth semi-rigid plastic. However, the shield can consist of any other material that can be smooth and semi-rigid such as polyethylene, polypropylene, vinyl, nylon, rubber, various impregnated or laminated fibrous materials, various plasticized materials, cardboard, paper, etc.

The shield is typically 1 mm to 4 mm in thickness, and has overall dimensions roughly 8.2 cm×10 cm (oblong shaped) with a 4.5 mm inside width. All outer edges 12, 16, 18, 22 and the edges of handle 10 of the shield are typically beveled or rounded to avoid snagging and personal injury.

Figure 2:
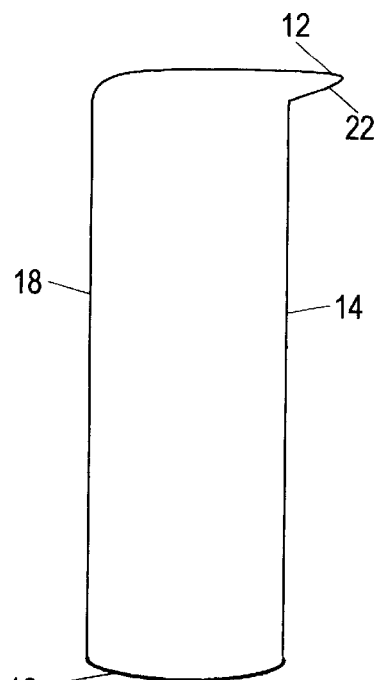
FIG. 2 shows a left side view of the shield constructed according to the invention.
Figure 3:
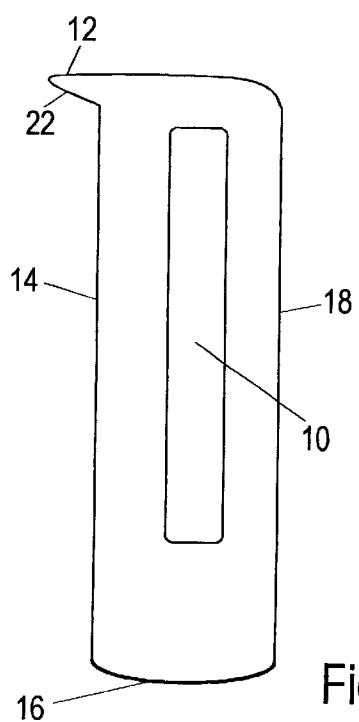
FIG. 3 shows a right view of the shield with handle constructed according to the invention.

Additional embodiments are shown in FIGS. 2 and 3. In FIG. 3 (right side view) handle 10 is perpendicular to the side 18. A handle 10 is typically 1 mm to 4 mm in thickness and roughly 5.5 cm×1.5 cm with typically a height of 2.5 mm. In FIG. 2 (left side view) shows the smooth exterior 14 and lip 22.

There are various possibilities with regards to the positioning and shape of handle, which is illustrated in FIG. 1 & 3. A handle 10 can be placed on either side of shield and can consist of any other shape that allows holding of shield.

Operation-FIGS. 1, 2, 3, 4

The manner of using this shield device is by inserting two fingers from the right hand into a handle 10 on the right side of device shown in FIG. 3 and lowering the shield between the legs until lip 22 as illustrated in FIG. 1 rests along inner thighs. In FIG. 4 interior 20 faces the urethra and back 14 faces episiotomy or perineum tear with top 12 held lightly against the skin between the vaginal opening and urethra. Whether sitting or standing sides 18 should be held vertically and bottom 16 should point downward thus urination may begin.

Summary, Ramifications, and Scope

Accordingly, the reader will see that the episiotomy or perineal tear shield of this invention can be used by females immediately after childbirth easily and conveniently, can be used without damaging the wound and can be portable. In addition, the shield can be made inexpensively of plastic and can be reusable or disposable

- it permits healing of the wound more quickly by protecting area from urine and infectious material;
- it allows use of shield by females anywhere;
- it permits use either standing or sitting;
- it permits a shield manufactured out of various materials both washable or disposable;
- it alleviates pain by eliminating urine contact to wound;

Although the description above contains many specificities, these should not be construed as limiting the scope of the invention but as merely providing illustrations of some of the presently preferred embodiments of this invention. For example, the shield can have different shaped handle, such as D-shaped, U-shaped, T-shaped, etc. The shield can consist of varied thickness, width, shape, length, etc, and the shield can be various colors or transparent.

Thus the scope of the invention should be determined by the appended claims and their legal equivalents, rather than by the examples given.

Having described my invention, what I claim as new and desire to secure is:

1. A shield device for use by females after childbirth for protecting episiotomy or perineal tear from urine while urinating, said device comprising a concave body having a contoured top lip whereby a user may place said contoured top lip against the user's skin between the vaginal opening and urethra to prevent the urine from contacting the episiotomy or perineal tear during urination.

2. The device as recited in claim 1 wherein said concave body is elongated with a spaced apart bottom and top and spaced apart sides and further comprises a handle adapted to be grasped by the user when placing said device against the user's skin.

3. The device as recited in claim 2 wherein said contoured top lip is adapted to contact at least one inner thigh of the user when placed against the user's skin between the vaginal opening and urethra.

4. The device as recited in claim 2 wherein the said contoured top lip is adapted to contact both inner thighs of the user when placed against the user's skin between the vaginal opening and urethra.

5. The device as recited in claim 2 wherein said body is chosen from the group including plastic, polyethylene, polypropylene, vinyl, nylon and rubber.

6. The device as recited in claim 2 wherein said body is made from a material chosen from the group including laminated fibrous materials such as cardboard, paper or the like.

7. A shield adapted to be used during urination to prevent urine exiting the urethra from contacting a proximate area, said shield comprising:

- an elongated body having a spaced apart top and bottom and spaced apart sides defining a concave interior therebetween;
- a contoured top lip integral with said body top, said lip having a beveled exterior surface;
- a handle integral with one of said sides; and,
- whereby a user may place said contoured top lip against the user's skin between the urethra and the proximate area to channel the urine along said concave interior to prevent contact with the proximate area.

8. The shield as recited in claim 7 wherein said contoured top lip is adapted to contact at least one inner thigh of the user when placed against the user's skin between the vaginal opening and urethra.

9. The shield as recited in claim 7 wherein the contoured top lip is adapted to contact both inner thighs of the user when placed against the user's skin between the vaginal opening and urethra.

10. The shield as recited in claim 7 wherein said body is chosen from the group including polyethylene, polypropylene, vinyl, nylon and rubber.

11. The shield as recited in claim 7 wherein said body is made from a material chosen from laminated fibrous materials such as cardboard, paper or the like.

12. The shield as recited in claim 7 wherein said top lip comprises a beveled exterior surface that is adapted to be held lightly against the skin adjacent the torn or cut area while said sides contact at least one of the user's inner thighs.

13. A shield adapted to be used during urination to prevent urine exiting the urethra from contacting an area torn or cut during childbirth, said shield comprising:

- an elongated body having a spaced apart top and bottom and spaced apart sides defining a concave interior therebetween;
- a contoured top lip integral with said body top, said lip having a beveled exterior surface that is adapted to contact both inner thighs of the user when placed against the user's skin between the urethra and the area torn or cut during childbirth to thereby provide a pathway along said concave interior for subsequent urine flow;
- a handle integral with one of said sides to facilitate user manipulation of said shield; and,
- whereby a user may place said contoured top lip against the user's skin between the urethra and the area torn or cut during childbirth to channel the urine along said concave interior to prevent contact with the area cut or torn during childbirth.

14. The shield as recited in claim 13 wherein said body is chosen from the group including polyethylene, polypropylene, vinyl, nylon and rubber.

15. The shield as recited in claim 13 wherein said body is made from a material chosen from laminated fibrous materials such as cardboard, paper or the like.

* * * * *